United States Patent
Son et al.

(10) Patent No.: US 11,954,855 B2
(45) Date of Patent: Apr. 9, 2024

(54) METHOD AND APPARATUS FOR EVALUATING DRUG

(71) Applicant: DAEGU GYEONGBUK INSTITUTE OF SCIENCE AND TECHNOLOGY, Daegu (KR)

(72) Inventors: Jong Wuk Son, Daegu (KR); Kook Rae Cho, Daegu (KR); Eun Joo Kim, Daegu (KR); Eun Sook Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 393 days.

(21) Appl. No.: 17/528,309

(22) Filed: Nov. 17, 2021

(65) Prior Publication Data
US 2022/0172352 A1 Jun. 2, 2022

(30) Foreign Application Priority Data
Nov. 30, 2020 (KR) .................. 10-2020-0164629

(51) Int. Cl.
*G06T 7/00* (2017.01)
*G06V 10/70* (2022.01)
(Continued)

(52) U.S. Cl.
CPC .......... *G06T 7/0012* (2013.01); *G06V 10/70* (2022.01); *G06V 20/69* (2022.01); *G16C 20/70* (2019.02);
(Continued)

(58) Field of Classification Search
CPC ......... G06T 7/0012; G06T 2207/20081; G06T 2207/30024; G06V 10/70; G06V 20/69;
(Continued)

(56) References Cited

U.S. PATENT DOCUMENTS 11,531,844 B2 * 12/2022 Bharti ................ G01N 15/1429
11,890,335 B2 * 2/2024 Mamula .................. A61P 35/00
(Continued)

FOREIGN PATENT DOCUMENTS

JP 6627069 1/2020
JP 2020166711 10/2020
(Continued)

OTHER PUBLICATIONS

Kobayashi et al., Label-free detection of cellular drug responses by high-throughput bright-field imaging and machine learning (Year: 2017).*

(Continued)

*Primary Examiner* — John B Strege
(74) *Attorney, Agent, or Firm* — LEX IP MEISTER, PLLC (57) ABSTRACT

Disclosed are a drug evaluation method and apparatus. The drug evaluation method includes acquiring cell images in response to a drug to be evaluated, loading an image processing-based learning model trained so as to predict molar concentrations, outputting molar concentrations of cells corresponding to the cell images by applying the learning model to the acquired cell images, and calculating a drug evaluation value used to evaluate effects of the drug (Continued)

on the cells based on the molar concentrations of the cells corresponding to the cell images output through the learning model.

18 Claims, 9 Drawing Sheets

(51) Int. Cl.
 *G06V 20/69* (2022.01)
 *G16C 20/70* (2019.01)
(52) U.S. Cl.
 CPC .............. *G06T 2207/20081* (2013.01); *G06T 2207/30024* (2013.01)
(58) Field of Classification Search
 CPC ........ G16C 20/70; G16C 20/30; G16C 20/60; G01N 33/5014; G06N 3/08; G06N 20/00
 See application file for complete search history.

(56) References Cited

U.S. PATENT DOCUMENTS

| | | | |
|---|---|---|---|
| 11,895,138 B1 * | 2/2024 | Talmor | ................ H04L 63/1433 |
| 2017/0076062 A1 * | 3/2017 | Choi | ...................... G16C 20/30 |
| 2017/0161469 A1 * | 6/2017 | Shibahara | .............. G16C 20/10 |
| 2019/0156933 A1 * | 5/2019 | Varshney | ................. G06N 3/08 |
| 2020/0311527 A1 * | 10/2020 | Tang | ...................... G06N 3/063 |
| 2023/0083769 A1 * | 3/2023 | Ma | ......................... G16H 20/10 |
| | | | 705/2 |

FOREIGN PATENT DOCUMENTS

| | | |
|---|---|---|
| KR | 10-1498481 | 3/2015 |
| KR | 10-2019-0080914 | 7/2019 |

OTHER PUBLICATIONS

Jimenez-Carretero et al. Tox_(R)CNN: Deep learning-based nuclei profiling tool for drug toxicity screening (Year: 2018).*
Zhixiong Zhang, "Cancer Drug Screening Scale-up: Combining Biomimetic Microfluidic Platforms and Deep Learning Image Analysis", Thesis, University of Michigan (Oct. 4, 2020).
KIPO, Office Action of Application No. 10-2020-0164629, dated Jul. 15, 2022.
Colleen M. Garvey et al., "A high-content image-based method for quantitatively studying context-dependent cell population dynamics", Scientific Reports, 6:29752, Jul. 25, 2016. DOI: 10.1038/srep29752.
Yanjing Zhu et al., "DeepScreen: An Accurate, Rapid, and Anti-Interference Screening Approach for Nanoformulated Medication by Deep Learning", Adv. Sci., vol. 5, issue 9, 1800909, Jul. 23, 2018. DOI: 10.1002/advs.201800909.
Shenghua He et al., "Deeply-supervised density regression for automatic cell counting in microscopy images", Medical Image Analysis, vol. 68, 101892 (Nov. 11, 2020). https://doi.org/10.1016/j.media.2020.101892.
KIPO, Office Action of KR 10-2020-0164629 dated Jan. 7, 2022.

* cited by examiner

METHOD AND APPARATUS FOR EVALUATING DRUG

CROSS-REFERENCE TO RELATED APPLICATION

This present application claims the benefit of priority to Korean Patent Application No. 10-2020-0164629, entitled "METHOD AND APPARATUS FOR EVALUATING DRUG," filed on Nov. 30, 2020, in the Korean Intellectual Property Office, the entire disclosure of which is incorporated herein by reference.

BACKGROUND OF THE INVENTION

Field of the Invention

The present disclosure relates to a drug evaluation method and apparatus in which efficacy and toxicity of a drug are evaluated using machine learning algorithm-based image processing technology.

Description of the Related Art

In general, the 50% inhibitory concentration (IC50) or the 50% effective concentration (EC50) is used to evaluate efficacy and toxicity of a drug in new drug development.

IC50 refers to the maximal concentration of a drug at a moment when enzyme or protein activity of cells is dropped by half in the case that the drug is injected into the cells. Here, an index indicating activity of the cells may vary, i.e., may be an enzyme or a protein, and thus, the value of IC50 may slightly vary in each test. Further, EC50 refers to the maximal concentration of a drug, which shows half of the maximum effect of the corresponding drug when the drug is injected into cells. EC50 may also be called "effective dose (ED50)". That is, these values are objective indexes which are representatively used to evaluate the effects of a specific drug on cells or a human body.

In order to determine IC50 and EC50, the MTT assay, the MTS assay and the CCK assay may be used, and in this case, after a specific cell line is treated with various concentrations of a drug and is cultured in a cell culture device, absorbances for colors obtained by treating the specific cell line with tetrazolium-based dyes, which stain only surviving cells, at an appropriate wavelength are measured.

Here, for example, 3-(4,5-dimethylthiazol-2-yl)-2,5-diphenyltetrazolium bromide may be used in the MTT assay, (3-(4,5-dimethylthiazol-2-yl)-5-(3-carboxymethoxyphenyl)-2-(4-sulfophenyl)-2H-tetrazolium may be used in the MTS assay, and 2-(2-methoxy-4-nitrophenyl)-3-(4-nitrophenyl)-5-(2,4-disulfophenyl)-2H-tetrazolium may be used in the CCK assay.

For example, a substance which may cause toxicity in the kidneys may be searched for using a biomarker protein which is expressed in cells with respect to a substance causing nephrotoxicity and side effects, as disclosed in Patent Document 1, and in this case, a concentration (i.e., IC50) of the substrate at which the substance causes toxicity in cells may be determined through the MTT assay.

In these conventional assays, it takes a reaction time of 3-4 hours for dyes to cause a reduction reaction due to oxidoreductases in living cells, and cells used once in the color reaction are not capable of being additionally cultured. Therefore, the cells are not capable of being used in subsequent tests, such as re-calculation of IC50/EC50 or a reaction mechanism after drug treatment, and it takes a long time and high costs to perform the assays because cell viability to drugs or various stresses must be determined through a separate assay process.

Further, washing of cells and injection of dyes are required during a process for performing the conventional assays, and this process may cause new test errors.

The above information disclosed in this Background section is only for enhancement of understanding of the background of the invention and therefore it may contain information that does not form the prior art that is already known in this country to a person of ordinary skill in the art.

RELATED ART DOCUMENT

Patent Document (Patent Document 0001) Korean Patent Registration No. 10-1498481 (Registration Date: Feb. 26, 2015)

SUMMARY OF THE INVENTION

Therefore, the present disclosure has been made in view of the above problems, and it is an object of the present disclosure to evaluate efficacy and toxicity of a specific drug using an image processing-based deep learning algorithm in which reaction of corresponding cells to the specific drug is output using cell images as inputs.

It is another object of the present disclosure to calculate cell viability to each of the concentrations of a drug without any separate treatment after a designated time from drug treatment, and to calculate an IC50 or EC50 value thereby.

It is still another object of the present disclosure to exclude a harmful tetrazolium-based substance from an experiment process so as to shorten an experiment time and to allow an additional experiment to be performed using cultured cells.

It is yet another object of the present disclosure to determine cell viability to various drugs and stresses without any separate assay process so as to reduce time and costs taken to perform the conventional MTT assay, MTS assay or CCK assay.

It is still yet another object of the present disclosure to continue cell culture after examination through a microscope so as to allow an experimenter to perform repeated measurement without damaging cells for a desired period.

It is a further object of the present disclosure to provide an interface configured to allow a method in which a pre-trained model is used and a method in which a user's own model is trained and then the trained model is used to be selectively applied depending on circumstances.

In accordance with an aspect of the present invention, the above and other objects can be accomplished by the provision of a drug evaluation method configured to evaluate efficacy and toxicity of a specific drug using an image processing-based deep learning algorithm in which reaction of corresponding cells to the specific drug is output using cell images as inputs.

The drug evaluation method may include acquiring cell images in response to a drug to be evaluated, loading an image processing-based learning model trained so as to predict molar concentrations, outputting molar concentrations of cells corresponding to the cell images by applying the learning model to the acquired cell images, and calculating a drug evaluation value used to evaluate effects of the drug on the cells based on the molar concentrations of the cells corresponding to the cell images output through the learning model.

Through the drug evaluation method, cell viability to each of the concentrations of the may be calculated without any separate treatment after a designated time from drug treatment, and thus, the measured value of an index to evaluate efficacy and toxicity of may be calculated, so as to reduce a time and costs taken to perform an experiment and to allow an additional experiment to be performed using cultured cells.

In accordance with other aspects of the present invention, there is provided other methods and systems for implementing the present invention and computer readable recording media provided with a computer program stored therein so as to execute the methods.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Advantages and features of the present invention and methods for achieving the same will become apparent from the descriptions of embodiments herein below with reference to the accompanying drawings.

However, the present invention is not limited to the embodiments disclosed below but may be implemented in various different forms, and it will be understood that the embodiments of the present invention are provided only to completely disclose the invention and cover modifications, equivalents or alternatives which come within the scope and technical range of the invention. The embodiments below are provided to make the description of the present invention thorough and to fully convey the scope of the present invention to those skilled in the art. In the following description of the present invention, a detailed description of known functions and configurations incorporated herein will be omitted when it may make the subject matter of the present invention rather unclear.

The terminology used herein is for the purpose of describing particular embodiments only and is not intended to be limiting. As used herein, singular forms may be intended to include plural forms as well, unless the context clearly indicates otherwise. The terms "comprising," "including," and "having" are inclusive and therefore specify the presence of stated features, integers, steps, operations, elements, components, and/or combinations thereof, but do not preclude the presence or addition of one or more other features, integers, steps, operations, elements, components, and/or combinations thereof. In the following description of the embodiments, terms, such as "first" and "second", are used only to describe various elements, and these elements should not be construed as being limited by these terms. These terms are used only to distinguish one element from other elements.

Hereinafter, reference will be made in detail to the embodiments of the present invention, examples of which are illustrated in the accompanying drawings. Some parts in one embodiment, which are substantially the same as those in other embodiments, will be denoted by the same reference numerals even though they are depicted in different drawings, and a detailed description thereof will thus be omitted because it is considered to be unnecessary.

Figure 1A:
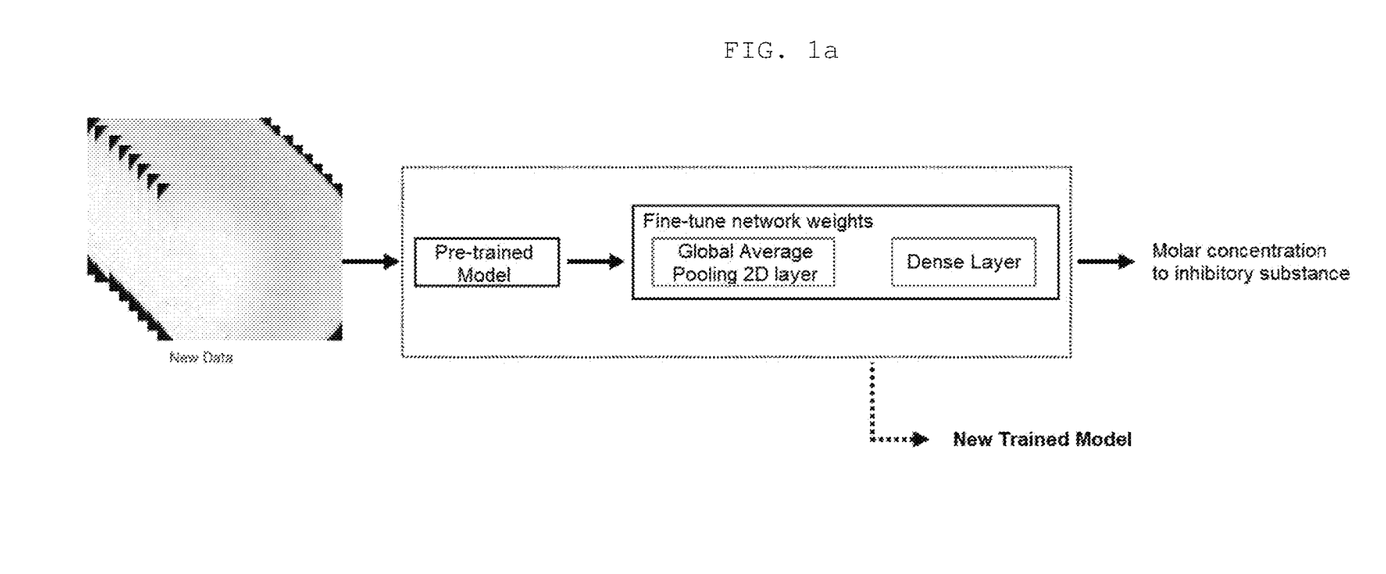
FIGS. 1a and 1b are views illustrating a learning model for evaluating a drug according to one embodiment of the present disclosure.
Figure 1B:
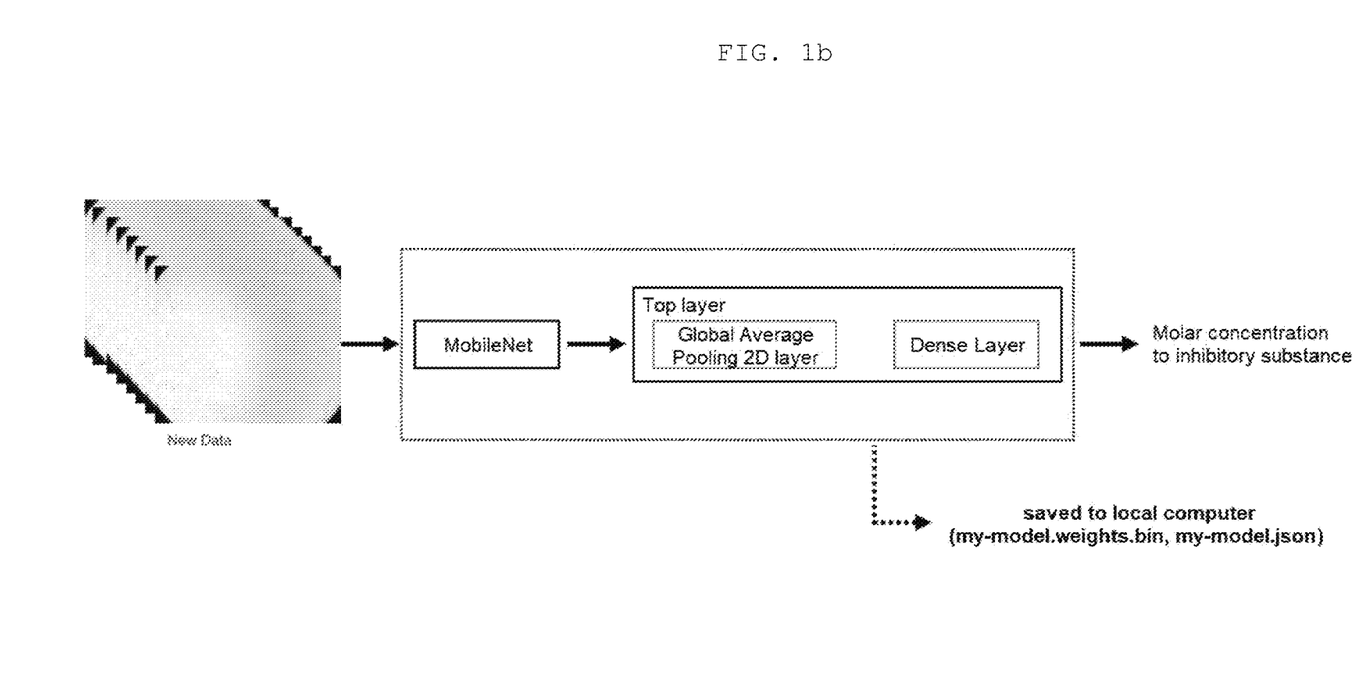

FIGS. 1a and 1b are views illustrating a learning model for evaluating a drug according to one embodiment of the present disclosure.

This embodiment relates to a method for detecting the effects of a specific drug on cells or a human body, in order to evaluate the efficacy, toxicity, etc. of the drug (for example, in a situation, such as new drug development or the like). As indexes of evaluation of efficacy and toxicity of drugs, there are the 50% inhibitory concentration (IC50), the 50% effective concentration (EC50), etc. Here, IC50 refers to the maximal concentration of a drug at a moment when enzyme or protein activity of cells is dropped by half in the case that the drug is injected into the cells. Here, an index indicating activity of the cells may vary, i.e., may be an enzyme or a protein, and thus, the value of IC50 may slightly vary in each test. Further, EC50 refers to the maximal concentration of a drug, which shows half of the maximum effect of the corresponding drug when the drug is injected into cells. EC50 may also be called "the effective dose (ED50)".

In this embodiment, IC50 will be described as an index used to evaluate the efficacy and toxicity of a drug. That is, in this embodiment, in order to determine IC50, molar concentrations may be predicted from cell images using deep learning-based image processing technology, and IC50 may be derived based thereon.

Particularly, in this embodiment, a pre-trained model may be used, as shown in FIG. 1a, and a custom model may be generated and used, as shown in FIG. 1b.

In more detail, in the method in which the pre-trained model is used, as shown in FIG. 1a, a new trained model may be generated by additionally applying a fine tuning algorithm (for example, fine-tuned network weights) to the pre-trained model, and the molar concentrations of cells to a drug may be output using the new trained model. Further, in the method in which the custom model is used, as shown in FIG. 1b, a known machine learning algorithm (for example, MobileNet, ResNet or the like) may be used, and the custom model trained such that the molar concentration of cells to a drug is output by providing fine tuned layers for finely adjusting weights at top layers.

Figure 2:
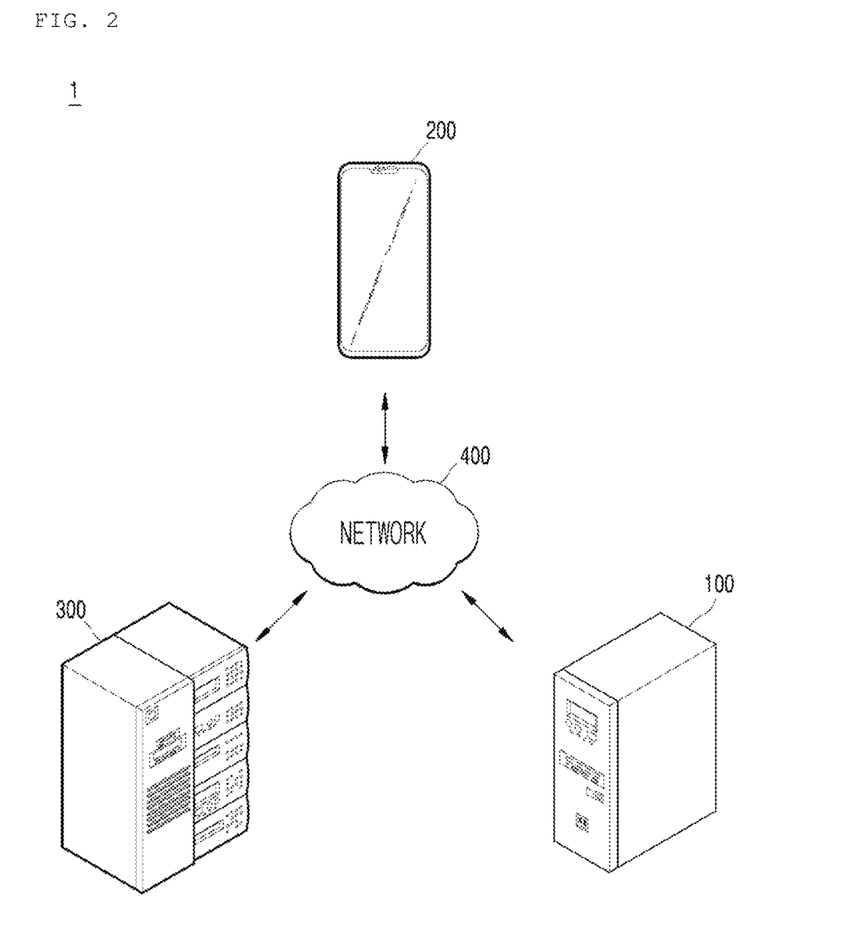
FIG. 2 is an exemplary view schematically illustrating a drug evaluation system according to one embodiment of the present disclosure.
Figure 3:
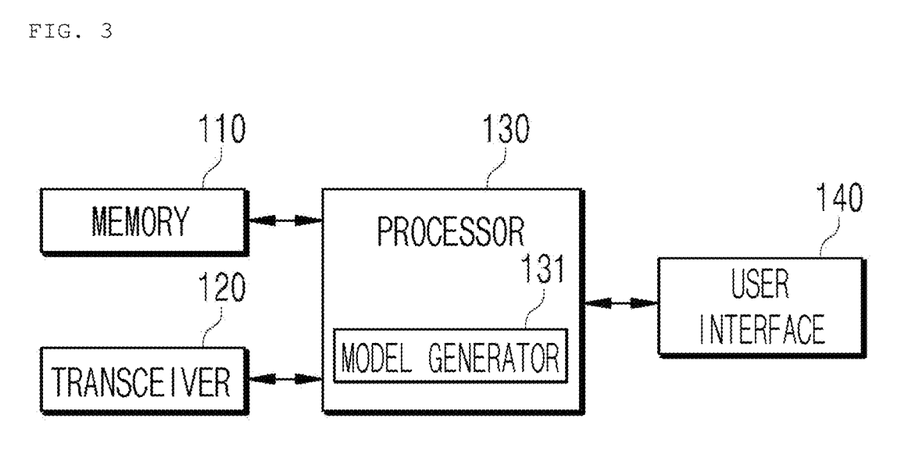
FIG. 3 is a block diagram schematically illustrating a drug evaluation apparatus according to one embodiment of the present disclosure.

FIG. 2 is an exemplary view schematically illustrating a drug evaluation system according to one embodiment of the present disclosure, and FIG. 3 is a block diagram schematically illustrating a drug evaluation apparatus according to one embodiment of the present disclosure.

As shown in FIG. 2, a drug evaluation system 1 may include a drug evaluation apparatus 100, a user terminal 200, a server 300 and a network 400.

In this case, in this embodiment, a user may access an application or a website implemented by the user terminal 200, and may perform a process, such as input of cell images for drug evaluation or generation of a customer model. That is, a series of processes shown in FIGS. 1a and 1b may be implemented in the application or the website of the user terminal 200. The user terminal 200 may provide a drug evaluation service through an authentication process after access to a drug evaluation application or a drug evaluation website. The authentication process may include authentication through input of user information, authentication through the user terminal 200, etc., without being limited thereto, or the authentication process may be performed just by accessing a link transmitted from the drug evaluation apparatus 100 and/or the server 300.

In this embodiment, the user terminal 200 may be a desktop computer, a smartphone, a notebook, a tablet PC, a smart TV, a mobile terminal, a personal digital assistance (PDA), a laptop, a media player, a micro server, a global positioning system (PGS), an electronic book terminal, a digital broadcasting terminal, a navigation system, a kiosk, an MP3 player, a digital camera, a home appliance or another mobile or non-mobile computing device which is operated by the user, but is not limited thereto. Further, the user terminal 200 may be a wearable terminal, such as a watch, glasses, a hairband or a ring which has a communication function and a data processing function. The user terminal 200 is not limited to the above description, and may be any terminal which can perform web browsing, without limitation.

In this embodiment, the drug evaluation system 1 may be implemented by the drug evaluation apparatus 100 and/or the server 300.

As shown in FIG. 3, the drug evaluation apparatus 100 may include a memory 110, a transceiver 120, a processor 130 and a user interface 140.

The memory 110 may store various pieces of information necessary to operate the drug evaluation apparatus 100 and store control software executed to operate the drug evaluation apparatus 100, and may include a volatile or non-volatile recording medium.

The memory 110 is connected to one or more processors 130, and may store code configured to cause the processor 130 to control the drug evaluation apparatus 100 when the memory 110 is operated by the processor 130.

Here, the memory 110 may include a magnetic storage medium or a flash storage medium, but is not limited thereto. The memory 110 may include a built-in memory and/or an external memory, and may include a volatile memory, such as a DRAM, an SRAM or an SDRAM, a non-volatile memory, such as a one time programmable ROM (OTPROM), a PROM, an EPROM, an EEPROM, a mask ROM, a flash RPM, a NAND flash memory or a NOR flash memory, a flash drive, such as an SSD, a compact flash (CF) card, an SD card, a micro-SD card, a mini-SD card, an xD card or a memory stick, or a storage device, such as an HDD.

Particularly, in this embodiment, the memory 110 may store a neural network model according to the present disclosure or a module configured to implement various embodiments of the present disclosure using the neural network model. Further, the memory 110 may store information related to an algorithm configured to perform learning according to the present disclosure. In addition, the memory 110 may store various pieces of information necessary in the range of achievement of the objects of the present disclosure, and the information stored in the memory 110 is received from the server 300 or an external device or is input by a user, and may thus be updated.

Here, the server 300 may be a server configured to operate the drug evaluation system 1 including the drug evaluation apparatus 100. Further, the server 300 may be a database server configured to provide big data necessary to apply various artificial intelligence algorithms and data necessary to operate the drug evaluation apparatus 100. In addition, the server 300 may include a web server or an application server configured to allow the drug evaluation system 1 to be implemented.

The transceiver 120 may provide a communication interface necessary to provide transmission and reception signals with external devices (including the server 300) in the form of packet data by interworking with the network 400. Further, the transceiver 120 may be a device including hardware or software necessary to transmit and receive signals, such as control signals or data signals, through wired and wireless communication with other network devices. The transceiver 120 may support various things intelligence communications (Internet of things (IoT), Internet of everything (IoE), Internet of small things (IoST), etc.), and may support machine-to-machine (M2M) communication, vehicle-to-everything (V2X) communication, device-to-device (D2D) communication, etc.

Here, the network 400 may perform a function of connecting the drug evaluation apparatus 100, the server 300 and the user terminal 200 to each other in the drug evaluation system 1. The network 400 may include, for example, a wired network, such as a local area network (LAN), a wide area network (WAN), a metropolitan area network (WAN) or an integrated service digital network (ISDN), or a wireless network, such as a wireless LAN, CDMA, Bluetooth or satellite communication, but is not limited thereto. Further, the network 400 may transmit and receive information using near field communication and/or long-range communication. Here, near field communication may include Bluetooth, radio frequency identification (RFID), infrared data association (IrDA), ultra-wideband (UWB), Zigbee and wireless fidelity (Wi-Fi) technologies, and long-range communication may include code division multiple access (CDMA), frequency division multiple access (FDMA), time division multiple access (TDMA), orthogonal frequency division multiple access (OFDMA) and single-carrier frequency division multiple access (SC-FDMA) technologies.

The network 400 may include connections of network elements, such as hubs, bridges, routers, switches and gateways. The network 400 may include one or more connected networks including a public network, such as the Internet, and a private network, such as a safe enterprise private network, for example, a multiple network environment. Access to the network 400 may be provided through one or more wired or wireless access networks. Further, the network 400 may support an Internet of things (IoT) network, in which distributed components, such as things, transmit and receive information therebetween so as to process the information, and/or 5G communication.

That is, the processor 130 may receive various data or information from an external device connected thereto through the transceiver 120, and may transmit various data or information to the external device. Further, the transceiver 120 may include at least one of a Wi-Fi module, a Bluetooth module, a wireless communication module or an NFC module.

The user interface 130 may include an input interface configured to collect various cell images applied to the drug evaluation apparatus 100 so as to evaluate a drug and configured to input a user request and commands for evaluating the drug therethrough. The cell images may be input by the user or may be obtained from the server 300.

Further, the user interface 140 may include an output interface configured to output results of evaluation performed by the drug evaluation apparatus 100 therethrough. For example, the molar concentrations of cells corresponding to the concentrations of the drug to be evaluated and a drug evaluation result may be output through the output interface. That is, the user interface 140 may output results in response to the user request and the commands for evaluating the drug.

The input and output interfaces of the user interface 140 may be implemented as the same interface, and in this embodiment, the detailed description of the user interface 140 provided to evaluate the drug will be described with reference to FIGS. 4 to 7.

Figure 4:
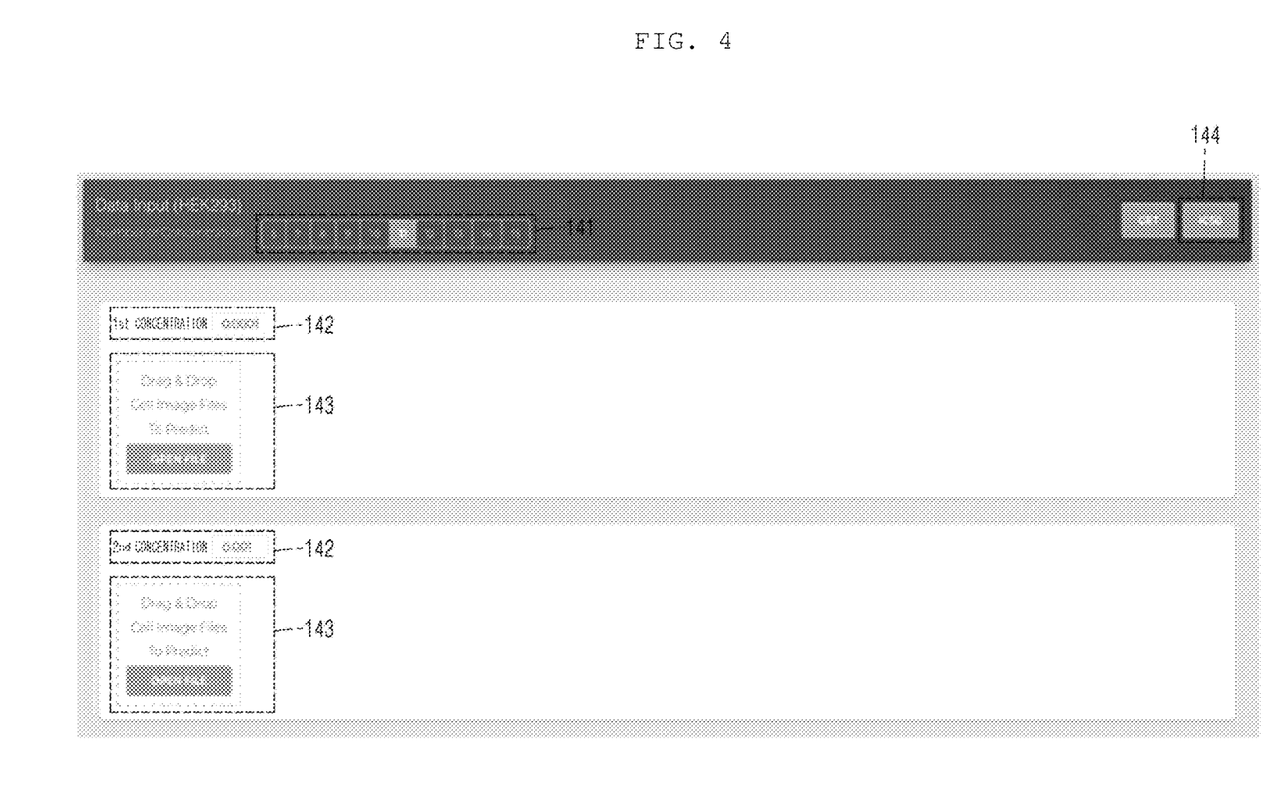
FIG. 4 is an exemplary view illustrating a process for inputting data in a drug evaluation interface according to one embodiment of the present disclosure.
Figure 5:
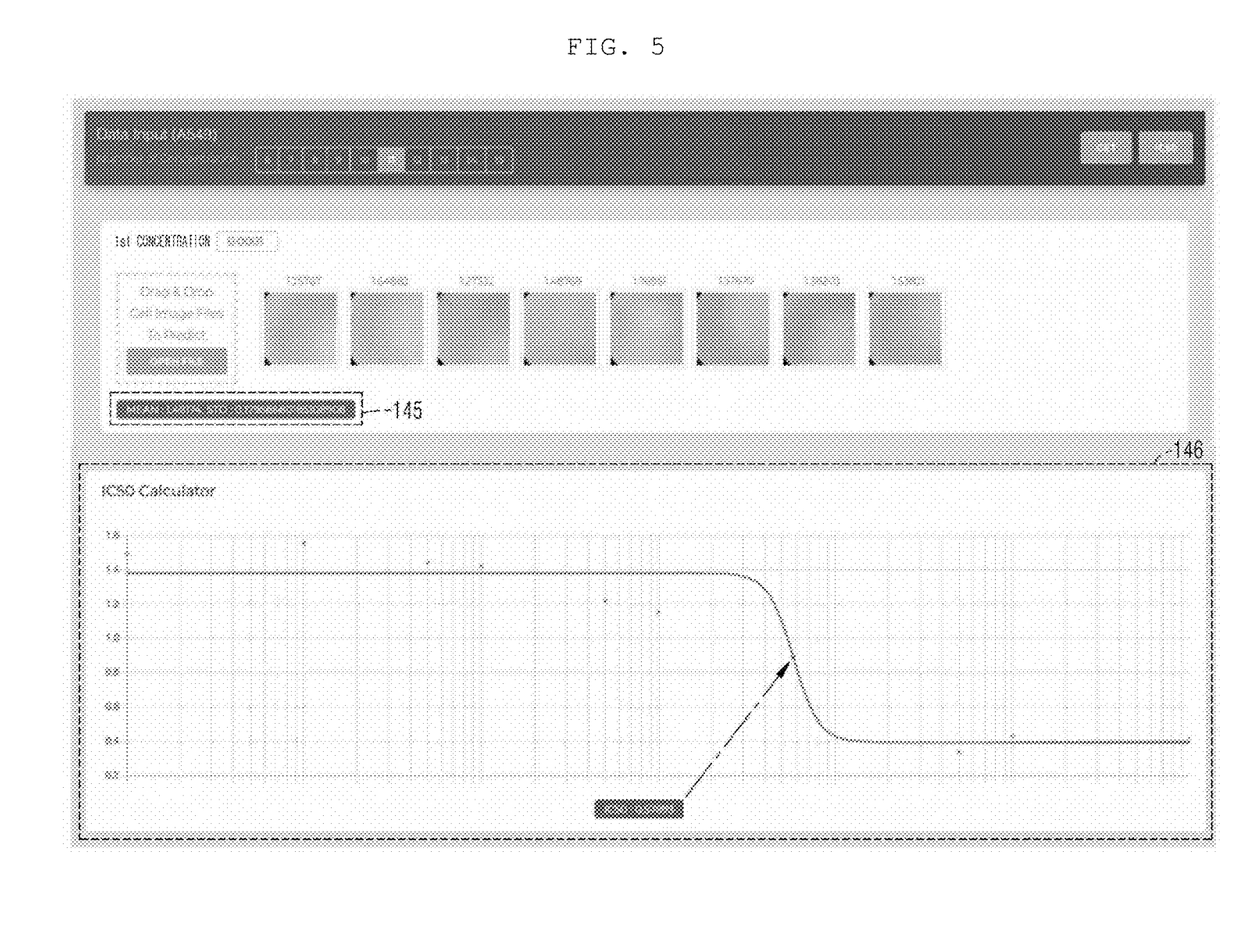
FIG. 5 is an exemplary view illustrating a process for outputting a result in the drug evaluation interface according to one embodiment of the present disclosure.
Figure 6:
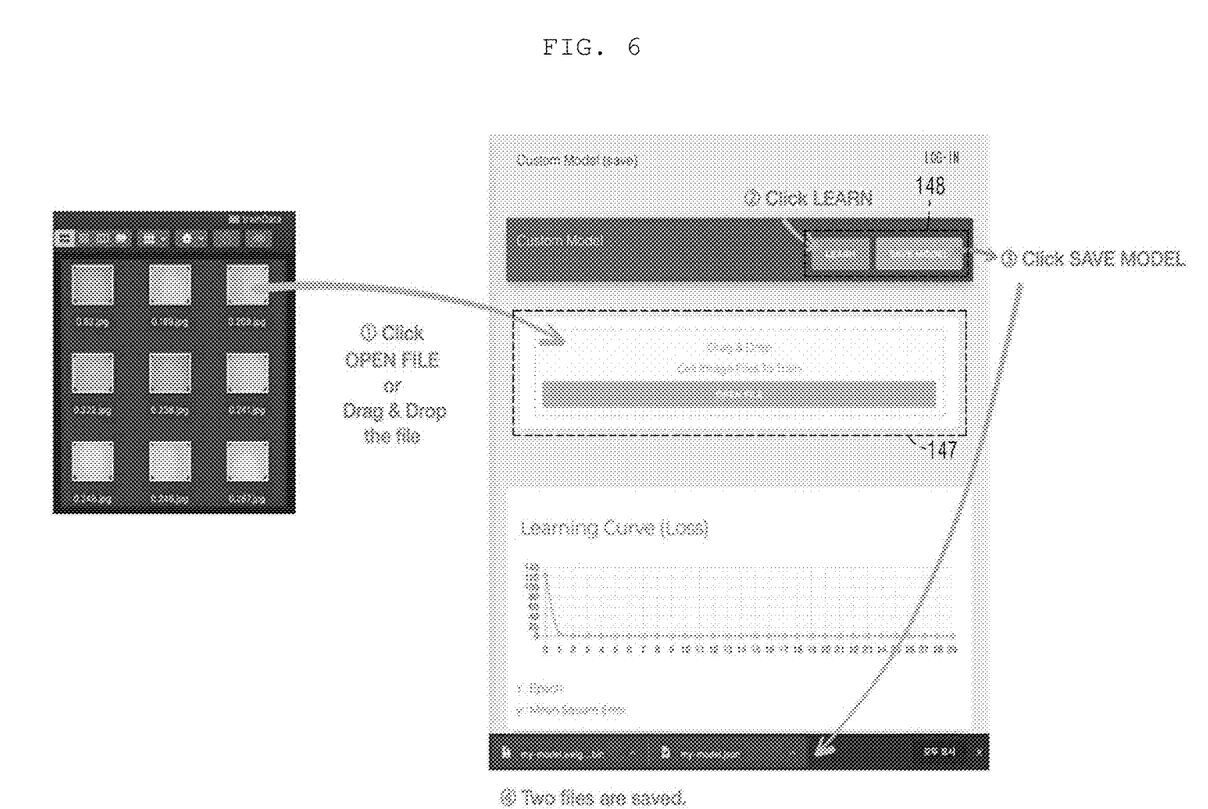
FIG. 6 is an exemplary view illustrating a process for generating a learning model in the drug evaluation interface according to one embodiment of the present disclosure.
Figure 7:
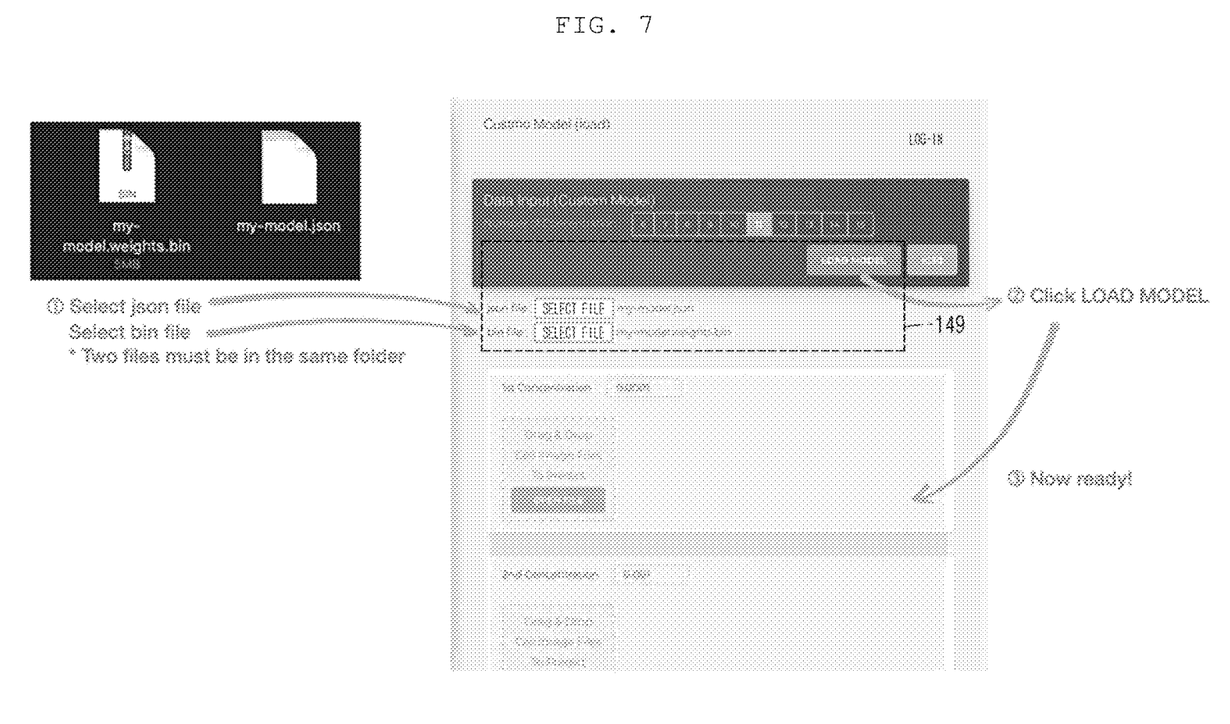
FIG. 7 is an exemplary view illustrating a process for loading the learning model in the drug evaluation interface according to one embodiment of the present disclosure.

FIG. 4 is an exemplary view illustrating a process for inputting data in the drug evaluation interface according to one embodiment of the present disclosure, FIG. 5 is an exemplary view illustrating a process for outputting results in the drug evaluation interface according to one embodiment of the present disclosure, FIG. 6 is an exemplary view illustrating a process for generating a learning model in the drug evaluation interface according to one embodiment of the present disclosure, and FIG. 7 is an exemplary view illustrating a process for loading the learning model in the drug evaluation interface according to one embodiment of the present disclosure.

Here, FIG. 4 illustrates an interface screen provided to input cell images when a pre-trained model is used, FIG. 5 illustrates an interface screen provided to output a drug evaluation result, FIG. 6 illustrates an interface screen provided to generate a custom model, and FIG. 7 illustrates an interface screen provided to load the custom model. That is, the interface for drug evaluation according to this embodiment shown in FIGS. 4 to 7 may be divided into the case that the pre-trained model is used and the case that the custom model is used, but may be implemented in the same manner in some embodiments.

In this embodiment, in a drug evaluation application or website, a learning model, which has been generated in advance and stored using TensorFlow JS, may be loaded and the molar concentration of cell images input by a user may be predicted. TensorFlow JS is a platform enabling TensorFlow, which is open source software for machine learning, to be implemented in an application or a website, and TensorFlow JS is just one embodiment and the present disclosure is not limited thereto.

As shown in FIG. 4, the user interface 140 according to this embodiment may include a drug concentration number setter 141 configured to set the number of the concentrations of a drug to be evaluated, a drug concentration inputter 142 configured to input the respective concentrations of the drug depending on the set number of the concentrations of the drug to be evaluated, a cell image inputter 143 configured to input cell images corresponding to the concentrations of the corresponding drug, and a result requester 144 configured to request output of results so as to predict the molar concentrations of cells through the learning model after input of the cell images in response to all the concentrations of the drug.

Here, the molar concentrations of the cells may indicate degrees of reaction in the cells to the drug.

Further, as shown in FIG. 5, the user interface 140 according to the present invention may include a molar concentration outputter 145 configured to output the molar concentrations of the cells in the respective cell images corresponding to the concentrations of the drug, means and standard deviations, and a drug evaluation outputter 146 configured to output the evaluation value (for example, IC50) of the drug based on the molar concentrations. Here, the molar concentrations depending on the concentrations of the drug are shown in a graph, and thereby, the maximal concentration of the drug at a moment when activity of the cells is dropped by half in the case that the drug is injected into the cells may be intuitively detected.

Further, as shown in FIG. 6, the user interface 140 according to this embodiment may include a data set inputter 147 configured to input data sets, each of which has a target cell image for generating the learning model and the molar centration of the target cell image as a label, and a model generation requester 148 configured to request generation of the learning model after input of all the data sets. For example, in this embodiment, the data sets may be uploaded through the data set inputter 147 (①), the learning model may be trained through the model generation requester 148 (②), and then, the trained learning model may be stored (③). Here, in this embodiment, the molar concentrations are labelled as the file names of the cell images, and thereby, support sets may be uploaded just by uploading the cell images. That is, when the molar concentration of a cell image is 0.838, the file name of the corresponding cell image may be set to 0.838.jpg. Further, in this embodiment, when the LEARN button is pressed through the model generation requester 148 so as to train the model, the model may be trained using the input cell images and the file names thereof set as the labels in the application or the website. Further, in this embodiment, when all training data is input by the user and the model is trained with the training data and is then stored, trained top layers may be stored, and for example, a my-model weights.bin file regarding weights to the generated learning model and a my-model.json file regarding to the algorithm of the generated learning model may be stored.

Further, as shown in FIG. 7, the user interface 140 according to this embodiment may include a custom model loader 149 configured to load the generated custom model after generation of the custom model. Here, in this embodiment, for example, after the stored my-model weights.bin file and my-model.json file are selected (①), the generated custom model may be loaded (②), and learning for drug evaluation may be performed using the generated custom model (③).

The processor 130 may control the overall operation of the drug evaluation apparatus 100. In more detail, the processor 130 may be connected to the elements of the drug evaluation apparatus 100 including the above-described memory 110, and may control the overall operation of the drug evaluation apparatus 100 by executing at least one command stored in the above-described memory 110.

The processor 130 may be implemented using various methods. For example, the processor 130 may be implemented as at least one of an application-specific integrated circuit (ASIC), an embedded processor, a microprocessor, hardware control logic, a hardware finite state machine (FSM) or a digital signal processor (DSP).

The processor 130 is a kind of central processing unit (CPU), and may operate the control software loaded in the memory 110 so as to control the overall operation of the drug evaluation apparatus 100. The processor 130 may include all kinds of devices which may process data. Here, the term 'processor' may mean a data processor having a physically structured circuit and mounted in hardware so as to perform functions expressed in code included in a program or commands. The data processor mounted in hardware may include, for example, a microprocessor, a central processing unit (CPU), a processor core, a multiprocessor, an application-specific integrated circuit, a field programmable gate array (FPGA) or the like, but is not limited thereto.

In this embodiment, the processor 130 may perform machine learning, such as deep learning, with respect to the acquired cell images so that the drug evaluation apparatus 100 outputs optimum molar concentration results and/or an optimum drug evaluation result, and the memory 110 may store data used in machine learning, result data, etc.

That is, in this embodiment, the processor 130 may perform drug evaluation using deep learning-based image processing technology, and in more detail, may acquire cell images in response to a drug to be evaluated, and may load an image processing-based learning model trained so as to predict molar concentrations.

The processor 130 may output the molar concentrations of cells corresponding to the cell images by applying the learning model to the acquired cell images, and may calculate the drug evaluation value used to evaluate the effects of the drug on the cells based on the molar concentrations of the cells corresponding to the cell images output through the learning model. Here, the learning model may be a learning model trained in a training phase including collecting cell images and molar concentration labels corresponding to the cell images, training an algorithm configured such that the cell images map to the molar concentration labels, and performing fine tuning by additionally inputting the cell images and the molar concentration labels corresponding to the cell images based on the trained algorithm. Here, the cell images and the molar concentration labels corresponding to the cell images may mean sets of actually measured data for training.

Here, fine tuning may mean transfer learning. In such transfer learning, performance of the model with respect to various tasks is improved using a deep neural network model, which has already been trained with bigger data sets having related tasks or characteristics, and for example, there are a fine tuning access method for one-shot video object segment in which the first frame is used, a method in which a model is temporarily updated using support data through fine tuning in the middle stage of the training phase and loss in each task is minimized, a method in which a fine tuning module is updated only in a fine tuning stage by separating learning of general knowledge and learning of knowledge capable of being transferred from each other, etc.

Further, in this embodiment, the learning model may be a learning model configured to have global average pooling (GAP) layers and dense layers at the rear ends of top layers of a pre-trained learning model and thus to be trained so as to update parameters, in order to perform fine tuning, and may be configured such that a mean squared error (MSE) loss function is applied to the learning model and MSE loss function-based optimization is performed through an adaptive moment estimation (Adam) optimization algorithm. Here, although this embodiment describes that the GAP layers, the dense layers, the MSE loss function and the Adam optimization algorithm are applied to one embodiment, they may not be applied to one embodiment.

In the conventional CNN architecture, features are extracted from input data via convolution layers and pooling layers and classification is performed using fully-connected (FC) layers at the end of the CNN, but the CNN architecture has a drawback in that overfitting easily occurs in the FC layers as the size of the CNN increases. As the width of the FC layers increases, the number of parameters increases and thus an environment in which overfitting easily occurs is created.

Therefore, in this embodiment, global average pooling (GAP) may be applied. GAP does not require use of FC layers when a vector having a size corresponding the number of classes at the end of a network so as to perform classification, and thus has advantages in that the number of parameters may be greatly reduced and overfitting may be prevented to some extent.

In such GAP, the depth of filters may be set to fit into the number of classes by performing 1×1 convolution on a final feature map obtained via the CNN architecture, and average pooling of the respective filters may be performed in units of one sheet. 1×1 convolution may be used to make the number of elements of an output vector and the number of the classes equal. That is, one value is output per two-dimensional filter, and thus, the number of the filters becomes equal to the number of the elements of the output vector using 1×1 convolution. The number of the elements of the output vector made through GAP is equal to the number of the classes, and thus, for example, SOFTMAX classification may be immediately performed.

Further, the dense layers may connect inputs and outputs, and may include weights configured to connect the inputs and the outputs respectively. The dense layers may be configured to design a model and to add layers.

Further, in this embodiment, an error of the learning model may be measured while the learning model is trained and a loss function may be minimized so that training of the learning model goes in the right direction, and in this embodiment, the MSE loss function may be applied as such a loss function.

The MSE loss function is a method for indicating how far away each data is from the mean, and a mean squared error (MSE) may be represented as the mean of the squares of errors (residuals) between an actual value and a predicted value. The MSE is a measure of evaluation as to whether or not the predicted value is similar to the actual value in order to evaluate predictive power of a regression model, and may be used as an index configured to grasp how much learning ability the learning model has through a difference between the actual value and the predicted value, and it may be considered that, as a result value decreases, evaluation is more accurate.

Further, an optimization algorithm may be applied in order to update parameters of the learning model based on the data and the loss function, and the Adam optimization algorithm applied in this embodiment is an optimization algorithm which may be used in place of the conventional stochastic gradient descent method so as to repeatedly update network weights based on training data.

The above-described model generation process may be summarized as follows. For example, images of cells to be analyzed may be input, and the molar concentrations corresponding to the corresponding cell images may be measured and collected as label data. Here, the molar concentrations used as labels may be acquired through the MTT assay, the MTS assay or the CCK assay which is known technology. Further, a deep learning-based learning model which uses the cell images as inputs and predicts the molar concentrations is generated, and in order to improve efficiency and accuracy in learning, a high-performance learning model which has already been trained, such as MobileNet or ResNet, may be reused as a pre-trained model. In this case, a regression model which may predict the molar concentrations may be finally generated by adding global average pooling 2D layers and dense layers to the rear end of the pre-trained model. Thereafter, weights of the global average pooling 2D layers and the dense layers may be trained using training data sets (including the cell images and the molar concentrations), and a final model including the pre-trained model, the global average pooling 2D layers and the dense layers may be generated.

In this embodiment, in order to evaluate a drug using the learning model, when cell images are acquired, a plurality of cell images at each of a plurality of concentrations of the drug may be acquired. That is, when the number of the concentrations of the drug to be evaluated is set and then the respective concentrations of the drug depending on the set number of the concentrations of the drug are input to the processor 130, the processor 130 may receive cell images corresponding to the input concentrations of the drug as inputs. For example, when the number of concentrations of the drug is eleven and the number of cell images capable of being input is eight, eight cell images corresponding to each of the concentrations of the drug may be input. For example, when the concentrations of the drug are set to 0.0001, 0.001, 0.005, 0.01, 0.05, 0.1, 0.5, 1, 5, 10 and 100, and eight cell images corresponding to each of the concentrations of the drug are acquired, 0.0001 µg/mL may be input as the value of the first concentration and eight cell images at the corresponding concentration may be input (with reference to FIG. 4).

When eight cell images in response to each of all the concentrations are input and a request to perform learning is received, molar concentrations may be predicted by the learning model, and in this case, both the cell images and the molar concentrations of the corresponding cell images may be output together. Further, the mean and the standard deviation of the molar concentrations may be output. For example, predicted molar concentration values may be output as 1.2567, 1.64882, 1.27332, 1.48768, 1.76951, 1.57670, 1.38203 and 1.53821, and the mean and the standard deviation of these values may be displayed.

That is, the processor 130 may output the mean value and the standard deviation values of the molar concentrations of cells corresponding to the cell images at each of the input concentrations of the drug.

Here, the processor 130 may exclude, among the cell images, cell images configured such that the respective output standard deviation values of the molar concentrations of the cells thereof are equal to or greater than a set value. That is, the processor 130 may exclude cell images corresponding to outliers by analyzing the output molar concentrations, and this operation may be automatically performed by the processor 130 or may be performed by allowing the user to exclude cell images determined as having molar concentration values greatly deviating from the mean by confirming the cell images and the output molar concentration values.

Further, although, in this embodiment, FIG. 5 illustrates that the mean values and the standard deviation values are output together with all the cell images at the respective concentrations of the drug, the cell images may be configured such that, when each of the cell images is selected, the molar concentration, the mean value and the standard deviation value of the selected cell image are output. Therefore, when the user excludes cell images corresponding to outliers, the user may select the cell images to be excluded by confirming the molar concentration of each of all the cell images and the mean value and the standard deviation value thereof by confirming each of all the cell images.

The processor 130 may calculate the drug evaluation value as the concentration of the drug when the mean value of the molar concentrations is a reference value, based on the mean value of the molar concentrations of the cell images at each of the concentrations of the drug. Here, in this embodiment, as shown in FIG. 5, a graph showing the mean of the predicted molar concentrations (represented by the y-axis) depending on the concentration of the drug (represented by the x-axis) may be output and, for example, the value of IC50 may be displayed on the graph. The concentration of a drug B at the moment when, on the assumption that the maximum degree of a reaction A is 100%, the degree of the reaction A is dropped to 50% using the drug B is referred to as IC50 of the drug B to the reaction A, and thus, the median on the graph may be output as IC50.

Further, the processor 130 may collects target cell images and molar concentration labels corresponding to the target cell images, when the performance of the learning model is not sufficient or no learning model is provided. That is, in this embodiment, not only the pre-trained learning model may be used, but also the custom model may be generated and used, and, when the performance of the learning model is not sufficient or no learning model is provided, for example, when accuracy of the learning model is calculated and the calculated accuracy of the learning model is low, the custom model may be generated.

Here, the case that the performance of the learning model is not sufficient may be the case that the accuracy of the learning model is less than a reference value or the number of data sets for training is less than a set number, or the case that training of the learning model is not sufficient or not complete, such as overfitting with respect to given data sets, and the set number may be changed by user settings or be set in the design stage.

In this embodiment, a test for accuracy calculation may be performed using test sets having cell images and molar concentrations corresponding to the cell images, and test sets may be determined by various methods, without being limited thereto.

The processor 130 may include a model generator 131, and when it is required to generate the custom model, the model generator 131 may generate a learning model in response to input of data sets from the user.

That is, in this embodiment, the custom model may be generated through the drug evaluation application or website by the user and the custom model may be used, because there are various kinds of cells and thus it is difficult to generate prediction models corresponding to all the cells in advance. Here, after the custom model is generated and loaded, the same process as for the above pre-trained learning model, i.e., acquiring a plurality of cell images at each of a plurality of different concentrations of a drug, results of training of the learning model using the acquired cell images, etc., may be performed.

For example, the model generator 131 may acquire cell images and molar concentrations for training the custom model, and may generate and store a learning model when all of the cell images and the molar concentrations for training are input (with reference to FIG. 6). Here, the model for training may be configured to have the same type as the pre-trained learning model, and may be configured such that the front end of the model includes MobileNet configured to provide high-speed learning and a high prediction speed in a web environment and the rear end of the model (i.e., top layers) includes global average pooling 2d layers and dense layers having one output. Here, when all training data is input by the user and the model is trained with the training data and is then stored, the model generator 131 may store trained top layers.

Further, in order to use the custom model to evaluate a drug, the stored custom model may be selected and loaded, and data for drug evaluation may be output by analyzing cell images based on the loaded custom model.

Figure 8:
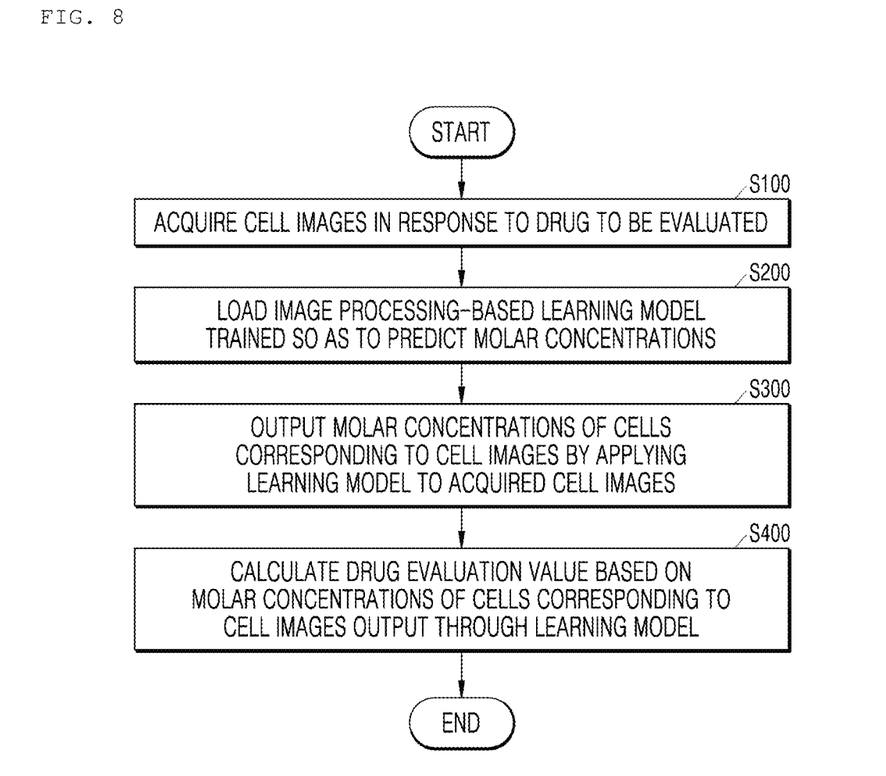
FIG. 8 is a flowchart illustrating a drug evaluation method according to one embodiment of the present disclosure.

FIG. 8 is a flowchart illustrating a drug evaluation method according to one embodiment of the present disclosure.

Referring to FIG. 8, in Operation S100, the drug evaluation apparatus 100 acquires cell images in response to a drug to be evaluated.

Here, the drug evaluation apparatus 100 may acquire a plurality of cell images at each of a plurality of concentrations of the drug. That is, when the number of concentrations of a drug to be evaluated is set and the concentrations of the drug depending on the set number of the concentrations of the drug are input to the drug evaluation apparatus 100, the drug evaluation apparatus 100 may receive cell images corresponding to the input concentrations of the drug as inputs.

In Operation S200, the drug evaluation apparatus 100 loads an image processing-based learning model trained so as to predict molar concentrations.

Here, the learning model may be a learning model trained in a training phase including collecting cell images and molar concentration labels corresponding to the cell images, training an algorithm configured such that the cell images map to the molar concentration labels, and performing fine tuning by additionally inputting the cell images and the molar concentration labels corresponding to the cell images based on the trained algorithm.

Further, in this embodiment, the learning model may be a learning model configured to have global average pooling (GAP) layers and dense layers disposed at the rear ends of top layers of a pre-trained learning model and thus to be trained so as to update parameters, in order to perform fine tuning, and may be configured such that a mean squared error (MSE) loss function is applied to the learning model and optimization is performed based on the MSE loss function through an adaptive moment estimation (Adam) optimization algorithm.

Particularly, in this embodiment, both the method in which the pre-trained model is used and the method in which the custom model is generated and used may be applied (with reference to FIG. 1). The method in which the pre-trained model is used and the method in which the custom model is generated and used are different in whether or not a process for generating the custom model using data sets of a user is performed, but may be executed in the same manner in which layers for fine tuning performed to finely adjust weights are provided at top layers. Layers for fine tuning are added at the rear of top layers of a known learning model algorithm in the pre-trained model, and layers for fine tuning are provided in the top layers in the custom model, but in the final learning model acquired by adding the layers for fine tuning to the pre-trained model, the layers for fine turning are provided in the top layers, and thus, the pre-trained model and the custom model may have the same configuration.

That is, the two methods are different just in a process of generating a learning model and then loading the learning model, and may be executed in the same manner through a process of inputting cell images so as to evaluate a drug, performing learning of the cell images and then outputting a result of learning, which will be described below in subsequent operations.

In Operation S300, the drug evaluation apparatus 100 outputs the molar concentrations of cells corresponding to the cell images by applying the learning model to the acquired cell images.

Thereafter, in Operation S400, the drug evaluation apparatus 100 calculates a drug evaluation value used to evaluate the effects of the drug on the cells based on the molar concentrations of the cells corresponding to the cell images output through the learning model.

That is, when the cell images corresponding to all the concentrations of the drug are input and a request to perform learning is received, the molar concentrations are predicted by the learning model, and in this case, the drug evaluation apparatus 100 may output both the cell images and the molar concentrations of the corresponding cell images. Further, the drug evaluation apparatus 100 may output a mean value and standard deviation values of the molar concentrations corresponding to the cell images at each of the input concentrations of the drug.

Finally, the drug evaluation apparatus 100 may calculate a drug evaluation value as the concentration of the drug when the mean value of the molar concentrations is a reference value, based on the mean values of the molar concentrations of the cell images at the respective concentrations of the drug. Here, in this embodiment, a graph showing the mean of the predicted molar concentrations (represented by the y-axis) depending on the concentration of the drug (represented by the x-axis) may be output (with reference to FIG. 5) and, for example, the value of IC50 may be displayed on the graph. That is, the drug evaluation value is intuitively output so that a drug evaluation result may be rapidly and accurately grasped just by inputting the cell images.

The above-described embodiment of the present invention may be implemented as a computer program which may be executed through various elements on computers, and the computer program may be recorded in computer readable recording media. Such computer readable recording media may include magnetic media, such as a hard disk, a floppy disk and a magnetic tape, optical recording media, such as a CD-ROM and a DVD, magneto-optical media, such as a floptical disk, and hardware devices configured to store and execute program commands, such as a ROM, a RAM and a flash memory.

The computer program may be specially designed for the present invention, or may be well known to those skilled in the art in the field of computer software. For example, the computer program may include not only machine code which is generated by a compiler but also high-level language code which is executable by a computer using an interpreter or the like.

In the description (particularly, the claims) of the present invention, the term "the" and indicative terms similar thereto may be intended to include singular and plural forms. In addition, it will be understood that, if a numerical range is disclosed in the description of the present invention, such a range includes all individual values within the range, unless stated otherwise.

The operations included in the method according to the present invention are not to be construed as necessarily requiring their performance in the particular order discussed or illustrated, unless specifically identified as an order of performance. The present invention is not limited as to the order in which the operations are written. All examples or exemplary terms (for example, etc.) in the description of the present invention are intended just to describe the present invention in detail, and do not limit the scope of the present invention, unless limited by the claims. Further, it should be apparent to those skilled in the art that various substitutions, changes and modifications which are not exemplified herein but are still within the spirit and scope of the present disclosure may be made.

Therefore, the scope of the present invention is defined not by the detailed description, but by the claims and their equivalents, and all variations within the scope of the claims and their equivalents are to be construed as being included in the present disclosure.

As is apparent from the above description of the present disclosure, an embodiment of the present disclosure provides a drug evaluation method and apparatus in which efficacy and toxicity of a specific drug may be evaluated using an image processing-based deep learning algorithm in which reaction of corresponding cells to the specific drug is output using cell images as inputs, thereby being capable of excluding a harmful tetrazolium-based substance from an experiment process so as to shorten an experiment time and to allow an additional experiment to be performed using cultured cells.

Further, cell viability to various drugs and stresses may be determined without any separate assay process, thereby being capable of reducing time and costs taken to perform the conventional MTT assay, MTS assay or CCK assay.

In addition, cell culture after examination through a microscope may be continued so as to allow an experimenter to perform repeated measurement without damaging cells for a desired period, thereby being capable of more effectively performing an experiment and thus improving user satisfaction.

Further, an interface may be provided so as to allow a method in which a pre-trained learning model is used and a method in which a user's own learning model is trained and then the trained learning model is used to be selectively applied depending on circumstances, thereby being capable of improving accuracy of the learning model.

Moreover, a regression model configured to predict molar concentrations may be generated as a final learning model by adding global average pooling 2D layers and dense layers to the learning model, and thereby, the performance of the final learning model may be improved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A drug evaluation method performed by a drug evaluation apparatus using deep learning-based image processing technology, the drug evaluation method comprising:
   acquiring cell images in response to a drug to be evaluated;
   loading an image processing-based learning model trained so as to predict molar concentrations;
   outputting molar concentrations of cells corresponding to the cell images by applying the learning model to the acquired cell images; and
   calculating a drug evaluation value used to evaluate effects of the drug on the cells based on the molar concentrations of the cells corresponding to the cell images output through the learning model.

2. The drug evaluation method according to claim 1, wherein the learning model is trained in a training phase comprising:
   collecting cell images and molar concentration labels corresponding to the cell images;
   training an algorithm configured such that the cell images map to the molar concentration labels; and
   performing fine tuning by additionally inputting the cell images and the molar concentration labels corresponding to the cell images based on the trained algorithm.

3. The drug evaluation method according to claim 2, wherein the learning model is configured to have a global average pooling (GAP) layer and a dense layer at rear end of top layers of a pre-trained learning model and is trained so as to update parameters, in order to perform fine tuning.

4. The drug evaluation method according to claim 2, wherein the learning model is configured such that a mean squared error (MSE) loss function is applied thereto and MSE loss function-based optimization is performed through an adaptive moment estimation (Adam) optimization algorithm.

5. The drug evaluation method according to claim 1, wherein the acquiring the cell images comprises:
   setting a number of concentrations of the drug to be evaluated;
   inputting the concentrations of the drug depending on the set number of the concentrations of the drug; and
   inputting cell images corresponding to the concentrations of the corresponding drug.

6. The drug evaluation method according to claim 5, wherein the outputting the molar concentrations of the cells corresponding to the cell images comprises outputting a mean value and standard deviation values of the molar concentrations of the cells corresponding to the cell images at each of the input concentrations of the drug,
   wherein the drug evaluation method further comprises excluding, among the cell images, cell images configured such that the respective output standard deviation values of the molar concentrations of the cells thereof are equal to or greater than a set value.

7. The drug evaluation method according to claim 6, wherein the calculating the drug evaluation value comprises calculating the drug evaluation value as a concentration of the drug when the mean value of the molar concentrations is a reference value, based on the mean value of the molar concentrations of the cell images at each of the concentrations of the drug.

8. The drug evaluation method according to claim 1, wherein the learning model is one of a custom model generated based on data collected by the drug evaluation apparatus and a learning model pre-trained by an external device and then provided to the drug evaluation apparatus.

9. The drug evaluation method according to claim 8, further comprising, when the learning model is the custom model generated by the drug evaluation apparatus:
   collecting target cell images and molar concentration labels corresponding to the target cell images; and
   generating the learning model based on the data collected by the drug evaluation apparatus.

10. A drug evaluation apparatus using deep learning-based image processing technology, comprising:
   a memory; and
   at least one processor connected to the memory and configured to execute computer readable commands included in the memory, wherein the at least one processor performs:

an operation configured to acquire cell images in response to a drug to be evaluated;

an operation configured to load an image processing-based learning model trained so as to predict molar concentrations;

an operation configured to output molar concentrations of cells corresponding to the cell images by applying the learning model to the acquired cell images; and an operation configured to calculate a drug evaluation value used to evaluate effects of the drug on the cells based on the molar concentrations of the cells corresponding to the cell images output through the learning model.

11. The drug evaluation apparatus according to claim 10, wherein the learning model is trained in a training phase comprising:

collecting cell images and molar concentration labels corresponding to the cell images;

training an algorithm configured such that the cell images map to the molar concentration labels; and performing fine tuning by additionally inputting the cell images and the molar concentration labels corresponding to the cell images based on the trained algorithm.

12. The drug evaluation apparatus according to claim 11, wherein the learning model is configured to have a global average pooling (GAP) layer and a dense layer at rear end of top layers of a pre-trained learning model and is trained so as to update parameters, in order to perform fine tuning.

13. The drug evaluation apparatus according to claim 11, wherein the learning model is configured such that a mean squared error (MSE) loss function is applied thereto and MSE loss function-based optimization is performed through an adaptive moment estimation (Adam) optimization algorithm.

14. The drug evaluation apparatus according to claim 10, wherein the operation configured to acquire the cell images is configured to perform:

an operation configured to set a number of concentrations of the drug to be evaluated;

an operation configured to input the concentrations of the drug depending on the set number of the concentrations of the drug; and an operation configured to input cell images corresponding to the concentrations of the corresponding drug.

15. The drug evaluation apparatus according to claim 14, wherein the operation configured to output the molar concentrations of the cells corresponding to the cell images is configured to perform an operation configured to output a mean value and standard deviation values of the molar concentrations of the cells corresponding to the cell images at each of the input concentrations of the drug, wherein the at least one processor is configured to further perform an operation configured to exclude, among the cell images, cell images configured such that the respective output standard deviation values of the molar concentrations of the cells thereof are equal to or greater than a set value.

16. The drug evaluation apparatus according to claim 15, wherein the operation configured to calculate the drug evaluation value is configured to perform an operation configured to calculate the drug evaluation value as a concentration of the drug when the mean value of the molar concentrations is a reference value, based on the mean value of the molar concentrations of the cell images at each of the concentrations of the drug.

17. The drug evaluation apparatus according to claim 10, wherein the learning model is one of a custom model generated based on data collected by the at least one processor and a learning model pre-trained by an external device and then provided to the drug evaluation apparatus.

18. The drug evaluation apparatus according to claim 17, wherein, when the learning model is the custom model generated by the at least one processor, the at least one processor is configured to further perform:

an operation configured to collect target cell images and molar concentration labels corresponding to the target cell images; and an operation configured to generate the learning model based on the data collected by the least one processor.

* * * * *